United States Patent [19]

Chabardes et al.

[11] Patent Number: 5,175,373
[45] Date of Patent: Dec. 29, 1992

[54] PROCESS FOR PREPARING CYCLOCITRAL

[75] Inventors: Pierre Chabardes, Sainte Foy Les Lyon; Bernard Delmond, Pessac; Claude Filliatre; Michel Pereyre, both of Talence; Dominique Serramedan, La Rochelle, all of France

[73] Assignee: Rhone-Poulenc Nutrition Animale, Commentry, France

[21] Appl. No.: 779,491

[22] Filed: Oct. 24, 1991

[30] Foreign Application Priority Data

Oct. 25, 1990 [FR] France .................................. 90 13249

[51] Int. Cl.⁵ ..................... C07C 47/058; C07C 47/04
[52] U.S. Cl. ...................................... 568/422; 568/420
[58] Field of Search .............................. 568/447, 446

[56] References Cited

U.S. PATENT DOCUMENTS 3,940,499  2/1976  Pittet et al. ........................... 568/447
3,956,393  5/1976  Pittet et al. ........................... 568/447
3,980,708  9/1978  Pittet et al. ........................... 568/447
4,000,131  12/1976  Rosenberger ....................... 568/447
4,026,824  5/1977  Pittet et al. ........................... 568/447

FOREIGN PATENT DOCUMENTS 0374509  6/1990  European Pat. Off. .
642962  5/1984  Switzerland .

OTHER PUBLICATIONS

A. Sevin et al., Bulletin De La Societe Chimique De France, No. 5-6, 1974, pp. 963-968, No. 188.
J. Ehrenfreund et al., Helvetica Chimica Acta, vol. 57, fasc. 4, No. 121, 1974, pp. 1098-1114.

Primary Examiner—Werren B. Lone
Attorney, Agent, or Firm—Finnegan, Henderson, Farabow, Garrett and Dunner

[57] ABSTRACT

A process for preparing cyclocitral by expoxidizing a pyronene.

18 Claims, No Drawings

PROCESS FOR PREPARING CYCLOCITRAL

BACKGROUND OF THE INVENTION

The present invention relates to a novel process for preparing cyclocitral. More particularly, it relates to a process for preparing cyclocitral from pyronene. The cyclocitral obtained constitutes an intermediate in the synthesis of vitamin A and may thus be used for this purpose.

A method for preparing cyclocitral from an unsaturated ketone involving the formation of an epoxide intermediate by means of a sulphur ylide is known in the prior art (Rosenberger et al., Helvetica Chemica Acta, Vol. 63, Fasc. 6 (1980)).

However, the starting ketone (trimethylcyclohexenone) is an expensive product and is difficult to obtain. This has effectively prevented industrial exploitation of the process.

Cyclocitral may also be prepared by cyclization of citralanil and hydrolysis of the protective amine group (Henbest et al., J. Chem. Soc., 1154 (1952)). However, this method requires multiple steps and involves the use of aniline, a toxic product.

Nothing in these documents teaches or suggests the possibility of preparing cyclocitral from pyronene. The process of the invention constitutes a novel means of producing cyclocitral which is particularly efficient and permits the production of cyclocitral from inexpensive and easily obtainable starting materials.

SUMMARY OF THE INVENTION

The process of the invention is characterized in that the following steps are carried out:

in a first step, a pyronene of formula (1)

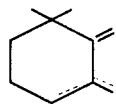

(1)

in which the dotted line represents only one double bond, which may thus be situated in the γ or δ position, is epoxidized; and, in a second step, the product obtained in the first step is converted to a cyclocitral of formula (2):

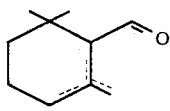

(2)

in which the dotted line has the same meaning as previously indicated, defining α, β or γ cyclocitral.

Thus, the starting reactants are 1,5,5-trimethyl-6-methylene-1-cyclohexene (γ-pyronene); and 1,1-dimethyl-2,3-dimethylenecyclohexane ($\delta^3$-pyronene).

Preferably, the starting pyronene is $\delta^3$-pyronene represented by the formula:

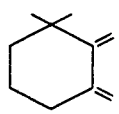

DESCRIPTION OF THE PREFERRED EMBODIMENTS

Reference will now be made in detail to the present preferred embodiments of the invention. In the examples and throughout the specification and claims, all parts and percentages are by weight unless otherwise specified.

The first step of the process is preferably carried out with an epoxidizing agent which may be selected from peracids or their derivatives, hydrogen peroxide, alkyl hydroperoxides, perborates or percarbonates.

The organic peracids which may be used in the present invention include optionally substituted aliphatic or aromatic carboxylic acids and acid derivatives. In particular, peracetic acid, performic acid, perpropionic acid, pertrifluoroacetic acid, paranitroperbenzoic acid or meta-chloroperbenzoic acid may be used.

Moreover, in one embodiment of the process of the invention, it is possible to directly synthesize the peracid "in situ" by using a mixture of hydrogen peroxide and a corresponding acid. In this case, the acid may be used in a catalytic amount since the starting acid is regenerated and may be recycled into a peracid by reacting with hydrogen peroxide during the reaction of the peracid with the pyronene.

The hydrogen peroxide may be used alone, in a basic medium or in combination with:

a metal; or a nitrile (Radziszewski's reaction: Wiberg, J. Amer. Chem. Soc., 75, 3961 (1953)).

Metals which are suitable for use in the process when hydrogen peroxide is used include transition metals such as tungsten, molybdenum, vanadium, titanium, platinum or manganese, any of which may be optionally combined with another metal such as tin. Preferably, tungsten, molybdenum or platinum are used as the transition metal.

In the case of alkyl hydroperoxides, the combination ROOH+ metal is used as an epoxidizing agent, in which R is an alkyl radical and the metal is selected from transition metals such as vanadium, titanium, molybdenum, platinum or cobalt.

Preferably, the alkyl hydroperoxide is represented by the formula:

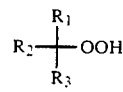

in which $R_1$ to $R_3$, which may be identical or different, each independently represents:

a hydrogen atom;

a linear or branched alkyl group containing 1 to 30 carbon atoms;

a cycloalkyl group containing 3 to 12 carbon atoms; or an alkyl- or cycloalkylaromatic group containing 7 to 30 carbon atoms.

Among the metals which may be used when the epoxidizing agent is an alkyl hydroperoxide, vanadium and titanium are preferred.

The epoxidation reaction may also be carried out in the presence of a perborate or a percarbonate. The percarbonates and the perborates which may be used in the present invention include sodium percarbonate (Chem Letters 665 (1986)), sodium perborate (Tetrahedron Letters, 2967 (1988)) and alkyl perborates (FR 1,447,267), whose effect on the epoxidation of alkenes has been described.

The epoxidation reaction is carried out in an inert medium in the presence of a solvent selected from:
water;
ethereal solvents such as ethyl or propyl ether, THF or alternatively methyl tert-butyl ether;
halogenated solvents such as chlorobenzenes, chloroform, methylene chloride or dichloropropane;
aliphatic or aromatic hydrocarbons, and in particular alkanes having more than 5 carbon atoms (hexane, heptane);
organic acids such as acetic acid or formic acid;
alcohols; or
esters.

The various reagents may be introduced simultaneously, but it is preferable to add the epoxidizing agent to the pyronene dissolved in a solvent.

It is also possible to add a phase transfer agent to the medium in order to perform the catalysis by phase transfer. In particular, the following may be added:
quaternary ammonium salts such as tetrabutylammonium hydroxide, bromide or chloride, methyltrioctylammonium chloride, dimethyl[dioctadecyl+dihexadecyl]ammonium chloride;
aromatic or chlorinated hydrocarbons;
phosphonium salts, such as hexadecyltributylphosphonium chloride;
certain anionic complexes such as tetrahexylammonium tetra(diperoxotungsto)phosphate.

The temperature of the reaction is preferably between $-30°$ C. and $+100°$ C., and even more preferably between $0°$ C. and $50°$ C. It may be particularly advantageous to carry out the reaction at about room temperature.

The molar ratio of epoxidizing agent/pyronene is preferably between 0.5/1 and 1.5/1 and more preferably about 1/1.

The reaction conditions (temperature, nature and amount of the solvent and the epoxidizing agent, and duration of the reaction) can readily be adjusted by a person skilled in the art to the desired optimum reaction rate and to the nature of the isomers sought.

During the first step of the process, the formation of the intermediate products of formula (3) occurs, in which the dotted line represents only one double bond:

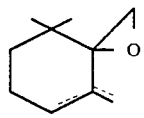

(3)

The products involved are thus 4,4-dimethyl-8-methylene-1-oxaspiro[2.5]octane and 4,8,8-trimethyl-1-oxaspiro[2.5]-4-octene, which may be purified.

During the first step of the process of the invention, various by-products of epoxidation may be formed. In particular, the following products have been isolated:

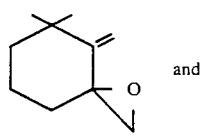

(4)

and

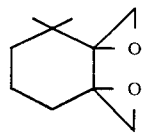

(5)

These by-products may optionally be separated from the products of formula (3) prior to the second step of the process by, for example, liquid phase chromatography. However, the second step of the process may also be carried out directly in the mixture formed in the first step. In this case, the cyclocitral of formula (2) can be isolated from the final product by any technique known to a person skilled in the art.

The second step of the process comprises converting the product obtained in the first step into the cyclocitral of formula (2).

Depending on the starting material and the reaction conditions, it is possible to selectively form the α, β or γ isomers of cyclocitral, which correspond to the three possible positions of the double bond.

This second step is carried out in the presence of a solvent which may be selected from among ethereal solvents such as ethyl or propyl ether, THF or alternatively methyl tert-butyl ether; halogenated solvents such as chlorobenzenes, chloroform, methylene chloride or dichloropropane; alkanes, particularly alkanes having more than 5 carbon atoms (hexane, heptane); organic acids such as acetic acid, formic acid or p-toluenesulphonic acid; alcohols; aromatic solvents or esters. It may be particularly advantageous to use the same solvent as in the first step.

The second step is preferably carried out under an inert atmosphere.

Various methods may be used to convert the intermediates to form the cyclocitral of formula (2). In particular, the conversion may be accomplished by heating, or by means of a catalyst, and, in particular, a metal or acid catalyst.

Several types of acid catalysts may be used, such as protonic acids (p-toluenesulphonic acid), Lewis acids (zinc bromide, magnesium bromide, alkylaluminates, boron trifluoride, aluminum chloride, zinc chloride, titanium chloride, tin chloride) or oxides (alumina).

In the case of metal catalysts, $MgBr_2$, $LiBF_4$, $BF_3.OEt_2$, or various transition metals such as palladium complexes, molybdenum or rhodium may be used in particular. It is also possible to use other metals such as copper.

Finally, these various types of metal catalysts may be used on a carrier, such as graphite.

The temperature of the mixture during the conversion step is adjusted depending on the catalyst used. Preferably, where possible, the temperature is identical to that of the first step of the process.

The second step of the process may be carried out immediately after the first in the same reaction vessel or may instead be carried out after separation of the epoxide formed.

The starting pyronene used in the present invention may be obtained in various ways. In particular, it may be prepared from myrcene according to the following procedure disclosed in French Patent Application FR 9,002,724:
bringing the myrcene into contact with sulphur dioxide in the presence of a polymerization inhibitor, at a temperature of between 60° and 100° C. in order to form myrcenesulphone;

treating the myrcenesulphone in the presence of a strong acid containing less than 5% water in order to form cyclic sulpholene; and heating the cyclic sulpholene, optionally in the presence of a basic catalyst, in order to form the pyronene.

During the second step, alkyl, aryl or halosulphonic acids, Nafion resins, perchloric acid, sulphuric acid or various heterogeneous acid catalysts may be used as strong acid.

The cyclocitral of formula (2) obtained according to the invention may be used as an intermediate in the synthesis of vitamin A (Chem. & Ind., p. 574 (1950); Chem. Letters, p. 1201 (1975)). It may also be used to prepare safranal (Tetrahedron Letters 36, p. 3175 (1974)).

The invention will be more completely described by means of the following examples which shall be considered as illustrative and not restrictive of the invention.

EXAMPLE 1

This example involves the synthesis of the epoxide of $\delta^3$-pyronene. 2.5 g of pyronene were diluted in 100 ml of anhydrous ether in a 250-ml enamelled pot under $N_2$ and at 0° C. 4 g of meta-chloroperbenzoic acid (80–90%) were then added. The mixture was allowed to equilibrate to room temperature and the stirring was maintained for 48 hours.

The mixture was diluted with 50 ml of ether, washed with a 10% solution of sodium bisulphite (2×50 ml) and then with a saturated solution of sodium bicarbonate (4×50 ml). It was dried over $MgSO_4$ and the solvent evaporated. If any acid remained, the mixture was taken up in a small amount of pentane and filtered. It was purified on $Al_2O_3$ (6% $H_2O$): eluent petroleum ether or pentane/ether, 9/1.

1.7 g of epoxide were obtained (yield=60%).

EXAMPLE 2

25 g of $Al_2O_3$, active grade I (MERCK), 30 ml of anhydrous ether and 1 g of the $\delta^3$-pyronene epoxide prepared as in Example 1 were introduced into a 50-ml round-bottomed flask under vigorous stirring and placed under $N_2$. The mixture was protected from light and a small amount of hydroquinone was added as a precaution. The mixture was stirred for 15 hours at room temperature. 20 ml of ether were added and the mixture again stirred for 15 minutes.

It was filtered, the filtrate was rinsed with 100 ml of ether, 100 ml of $CHCl_3$ and 100 ml of a 1:1 ether:methanol mixture. The solvents were evaporated.

A crude product with a VPC titre of:
α-cyclocitral: 4%
β-cyclocitral: 84%
γ-cyclocitral: 12%
was obtained with a yield of 94%.

EXAMPLE 3

0.5 ml of $Br_2$ were added at 10° C. to 750 mg of Mg chips in 35 ml of anhydrous ether in a 100-ml enamelled pot equipped with a condenser, with magnetic stirring and placed under $N_2$.

After half an hour, the mixture was refluxed for 5 hours and then allowed to stand overnight at room temperature and under $N_2$. 500 mg of $\delta^3$-pyronene epoxide were then added in 15 ml of anhydrous benzene. The mixture was refluxed for 1 hour. The mixture was allowed to equilibrate to room temperature. It was then hydrolyzed on ice and washed to neutrality with a saturated solution of $NH_4Cl$. It was dried over $MgSO_4$ and the solvents were evaporated. A crude product with the following VPC titre:

γ-cyclocitral: 88% was obtained with a yield of 98%.

EXAMPLE 4

890 mg (3.95 mmol) of zinc bromide dissolved in 50 ml of benzene and under $N_2$ were placed in a 100-ml round-bottomed flask.

500 mg (3.29 mmol) of δ-pyronene epoxide dissolved in a few milliliters of benzene were added. The mixture was refluxed for 45 minutes and then allowed to equilibrate to room temperature. It was hydrolyzed on ice and washed to neutrality with a saturated solution of $NH_4Cl$. The aqueous phases were then extracted with 2×50 ml of ether. The mixture was dried over $MgSO_4$ and the solvents evaporated.

420 mg of crude product were obtained.

After purification on a deactivated $Al_2O_3$ column (6% $H_2O$) the following were obtained with a yield of 84%:

α-cyclocitral preponderant: 86%
γ-cyclocitral: 14%

EXAMPLE 5

300 mg (1.97 mmol) of δ-pyronene epoxide in 15 ml of anhydrous benzene were placed in a 30-ml round-bottomed flask. 94 mg (0.4 mmol) of p-toluenesulphonic acid were then added.

The mixture was refluxed for 3 hours and then allowed to equilibrate to room temperature. It was hydrolyzed on ice, extracted with ether, washed with a saturated solution of sodium bicarbonate and dried over magnesium sulphate. After evaporation of the solvents, 285 mg of a mixture of β and γ isomers, which were assayed by capillary VPC, were obtained:

β-cyclocitral: 90%
γ-cyclocitral: 10%
Yield=95%.

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

what is claimed is:

1. A process for preparing cyclocitral, comprising the steps of:

a) epoxidizing a pyronene represented by formula (1)

(1)

in which the dotted line represents only one double bond; and thereafter, b) converting the product from the first step into a cyclocitral represented by formula (2)

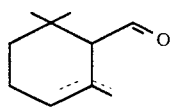

(2)

in which the dotted lines in both formulas (1) and (2) represent only one double bond, wherein the pyronene is epoxidized by an epoxidizing agent selected from peracids and their derivatives, hydrogen peroxide, alkyl hydroperoxides, perborates and percarbonates, and wherein the epoxidation reaction is carried out in an inert medium in the presence of a solvent selected from the group consisting of water, ethereal solvents, halogenated solvents, aliphatic hydrocarbons, aromatic hydrocarbons, organic acids, alcohols and esters.

2. The process of claim 1, wherein the pyronene is $\delta^3$-pyronene represented by the formula:

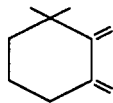

3. The process of claim 1, wherein the epoxidizing agent is a peracid and is an unsubstituted or a substituted aliphatic or aromatic carboxylic acid or a derivative thereof.

4. The process of claim 3, wherein the peracid is selected from the group consisting of peracetic, performic, perpropionic, pertrifluoroacetic, para-nitroperbenzoic and meta-chloroperbenzoic acids.

5. The process of claim 3, wherein the peracid is formed in situ during the epoxidizing step.

6. The process of claim 1, wherein the epoxidizing agent is hydrogen peroxide and is used alone, in a basic medium or combined with a nitrile or a metal.

7. The process of claim 1, wherein the epoxidizing agent is an alkyl hydroperoxide comprising the combination ROOH/metal, in which R is an alkyl radical and the metal is a transition metal.

8. The process of claim 7, wherein the alkyl hydroperoxide is represented by the formula:

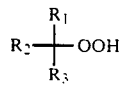

in which $R_1$ to $R_3$, which may be identical or different, each independently represents:
 a) a hydrogen atom;
 b) a linear or branched alkyl group containing 1 to 30 carbon atoms;
 c) a cycloalkyl group containing 3 to 12 carbon atoms; or,
 d) an alkyl- or cycloalkylaromatic group containing 7 to 30 carbon atoms.

9. The process of claim 7, wherein the transition metal is selected from tungsten, molybdenum, vanadium, titanium, platinum, manganese and cobalt.

10. The process of claim 6, wherein the hydrogen peroxide is used with a transition metal selected from tungsten, molybdenum and platinum.

11. The process of claim 9, wherein the transition metal is selected from vanadium and titanium.

12. The process of claim 1, wherein the reaction is carried out under an inert atmosphere and at a temperature of between $-30°$ C. and $+100°$ C.

13. The process of claim 12, wherein said temperature is between $0°$ C. and $50°$ C.

14. The process of claim 1, wherein the molar ratio of epoxidizing agent/pyronene is between 0.5/1 and 1.5/1.

15. The process of claim 15, wherein said molar ratio is about 1/1.

16. The process of claim 1, wherein in the second step, the product derived from the first step is heat treated, and/or treated in the presence of an acid or metal catalyst.

17. The process of claim 16, wherein the catalyst is an acid catalyst selected from protonic acids, Lewis acids and oxides.

18. The process of claim 16, wherein the catalyst is a supported metal catalyst.

* * * * *

UNITED STATES PATENT AND TRADEMARK OFFICE
CERTIFICATE OF CORRECTION

PATENT NO. : 5,175,373
DATED : December 29, 1992
INVENTOR(S) : Pierre Chabardes et al.

It is certified that error appears in the above-indentified patent and that said Letters Patent is hereby corrected as shown below:

Claim 1, column 7, first five lines, formula 2 change .

Claim 4, column 7, line 32, change "claim 3" to --claim 1--.

Signed and Sealed this

Twentieth Day of December, 1994

Attest:

BRUCE LEHMAN

Attesting Officer     Commissioner of Patents and Trademarks